(12) United States Patent
Fujieda

(10) Patent No.: US 7,506,980 B2
(45) Date of Patent: Mar. 24, 2009

(54) OPHTHALMIC APPARATUS

(75) Inventor: Masanao Fujieda, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 11/902,886

(22) Filed: Sep. 26, 2007

(65) Prior Publication Data

US 2008/0079899 A1 Apr. 3, 2008

(30) Foreign Application Priority Data

Sep. 29, 2006 (JP) .............................. 2006-266746

(51) Int. Cl.
*A61B 3/10* (2006.01)
(52) U.S. Cl. ..................... 351/205; 351/211
(58) Field of Classification Search ......... 351/205–212, 351/239–246
See application file for complete search history.

(56) References Cited

U.S. PATENT DOCUMENTS

| 5,500,697 A | * | 3/1996 | Fujieda ....................... 351/212 |
| 5,555,039 A | * | 9/1996 | Iki et al. ...................... 251/205 |
| 5,907,388 A | | 5/1999 | Fujieda ........................ 351/211 |
| 6,234,978 B1 | | 5/2001 | Mihashi et al. ............. 600/558 |

FOREIGN PATENT DOCUMENTS

| JP | A-02-302243 | 12/1990 |
| JP | A-09-187426 | 7/1997 |
| JP | A-10-108837 | 4/1998 |
| JP | A-10-216092 | 8/1998 |

* cited by examiner

*Primary Examiner*—Mohammed Hasan
(74) *Attorney, Agent, or Firm*—Oliff & Berridge, PLC

(57) ABSTRACT

An ophthalmic apparatus capable of easily checking opacity of a crystalline lens, and more appropriately evaluating a measurement result on eye refractive power distribution or wavefront aberration, which includes a measurement optical system for projecting measurement light onto a fundus of an examinee's eye and photo-receiving the measurement light reflected from the fundus so as to measure eye refractive power distribution or wavefront aberration, an illumination for an anterior segment, a first image-pickup optical system for picking up an image of the anterior segment, a projection optical system for projecting photographing light onto the fundus, a second image-pickup optical system for photo-receiving the photographing light so as to pick up a diaphanoscopic image, a monitor, a calculation part for obtaining a mapping image based on a result of the measurement, and a control part for displaying the mapping image and the diaphanoscopic image on one screen of the monitor.

8 Claims, 4 Drawing Sheets

OPHTHALMIC APPARATUS

BACKGROUND OF THE INVENTION

1. Field of the Invention

The present invention relates to an ophthalmic apparatus which measures eye refractive power distribution or wavefront aberration of an examinee's eye.

2. Description of Related Art

Conventionally, there is known an ophthalmic apparatus which measures eye refractive power distribution or wavefront aberration of an examinee's eye by projecting measurement light onto a fundus of the eye and photo-receiving the measurement light reflected from the fundus. Such an apparatus displays a measurement result on the eye refractive power distribution or the wavefront aberration as a mapping image (see U.S. Pat. No. 5,907,388 corresponding to Japanese Patent Application Unexamined Publication No. Hei10-108837). However, with such an apparatus, even when the mapping image shows an influence of opacity of a crystalline lens or other factors, it is difficult to check or locate the opacity of the crystalline lens or other factors which causes the influence.

In addition, there is known an eye refractive power measurement apparatus which measures eye refractive power of an examinee's eye, which has a function of picking up and displaying a diaphanoscopic image of the eye (see Japanese Patent Application Unexamined Publication No. Hei2-302243). However, the display of the diaphanoscopic image by such an apparatus is just used for checking in reliability of a measurement result on the eye refractive power, and does not enable checking variation of eye refractive power distribution and others of the examinee's eye caused by the an influence of the opacity of the a crystalline lens or other factors.

SUMMARY OF THE INVENTION

An object of the invention is to provide an ophthalmic apparatus capable of easily checking opacity of a crystalline lens or other factors, and more appropriately evaluating a measurement result on eye refractive power distribution or wavefront aberration.

To achieve the objects and in accordance with the purpose of the present invention, the ophthalmic apparatus includes a measurement optical system for projecting measurement light onto a fundus of an examinee's eye and photo-receiving the measurement light reflected from the fundus so as to measure eye refractive power distribution or wavefront aberration of the eye, an illumination for an anterior segment of the eye, a first image-pickup optical system for picking up an image of the anterior segment, a projection optical system for projecting photographing light onto the fundus, a second image-pickup optical system for photo-receiving the photographing light reflected from the fundus so as to pick up a diaphanoscopic image of the eye, a monitor, a calculation part for obtaining a mapping image based on a measurement result obtained by the measurement optical system, and a control part for displaying the mapping image and the diaphanoscopic image on one screen of the monitor.

Additional objects and advantages of the invention are set forth in the description which follows, are obvious from the description, or may be learned by practicing the invention.

The objects and advantages of the invention may be realized and attained by the ophthalmic apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
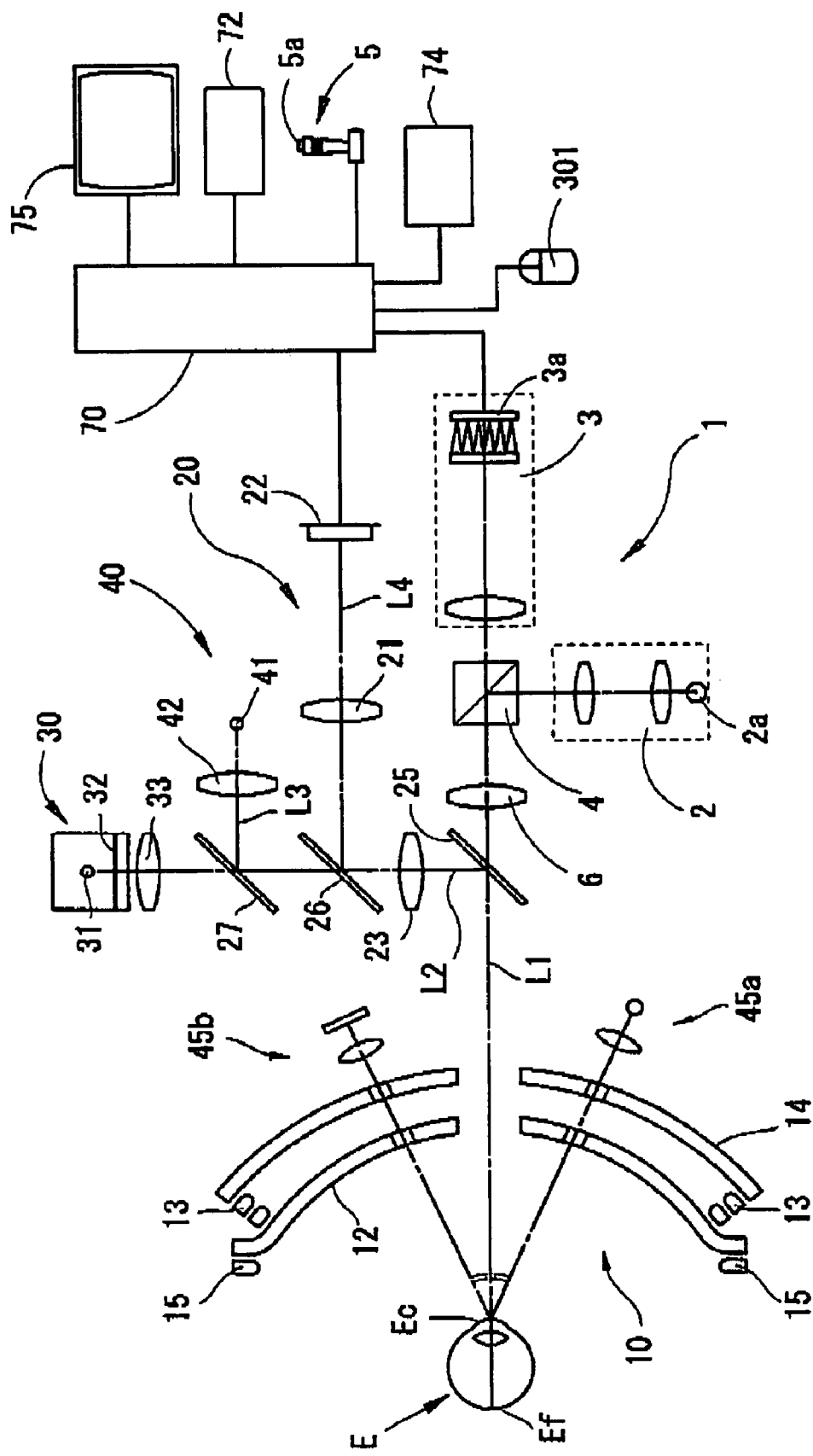
FIG. 1 is a view showing a schematic configuration of an optical system and a control system of an ophthalmic apparatus according to a preferred embodiment of the present invention.

A detailed description of one preferred embodiment of an ophthalmic apparatus embodied by the present invention is provided below with reference to the accompanying drawings. FIG. 1 is a view showing a schematic configuration of an optical system and a control system of the ophthalmic apparatus according to the preferred embodiment of the present invention.

The optical system of the apparatus according to the present invention includes an optical system 10 which projects a ring-pattern target onto a cornea Ec of an examinee's eye E, an optical system 20 which picks up an image of an anterior segment of the eye E, an optical system 30 which presents a fixation target to the eye E, an optical system 40 which projects a target for alignment in right-and-left and up-and-down directions (hereinafter, X and Y directions) onto the cornea Ec, and an optical system 45a which projects a target for alignment in a back-and-forth direction (hereinafter, a Z direction), which is a working distance direction of the apparatus, onto the cornea Ec, an optical system 45b which detects an image of the target for alignment in the Z direction, and an optical system 1 which measures eye refractive power distribution or wavefront aberration of the eye E.

The optical system 10 includes a placido ring plate 12 which has a number of light transmitting portions and light shielding portions which are concentrically arranged about an optical axis L1, infrared light sources 13, and a reflecting plate 14. Light from the light sources 13 is reflected by the reflecting plate 14, passes through the transmitting portions of the ring plate 12, and projects the ring-pattern target onto the cornea Ec.

The optical system 30, which is arranged on an optical axis L2 which is made coaxial with the optical axis L1 by a dichroic mirror 25, includes a visible light source 31, a fixation target plate 32, and a lens 33. Light from the light source 31 passes through the fixation target plate 32, is transmitted through the lens 33, a dichroic mirror 27, a half mirror 26, and an objective lens 23, is reflected by the dichroic mirror 25, and projects the fixation target onto a fundus Ef of the eye E. The light source 31 and the fixation target plate 32 are made movable in a direction of the optical axis L2, in order to fog the eye E by changing visibility of the fixation target.

The optical system 40, which is arranged on an optical axis L3 which is made coaxial with the optical axis L2 by the dichroic mirror 27, includes an infrared light source 41 and a lens 42. Light from the light source 41 is transmitted trough the lens 42, is reflected by the dichroic mirror 27, is transmitted through the half mirror 26 and the lens 23, is reflected by the dichroic mirror 25, and projects the target for alignment in the X and Y directions onto the cornea Ec.

The optical system 20, which is arranged on an optical axis L4 which is made coaxial with the optical axis L2 by the half mirror 26, includes an image-pickup lens 21 and a two-dimensional image-pickup element 22. Light from infrared light sources 15, which define an illumination for the anterior segment of the eye E, is reflected by the anterior segment and then by the dichroic mirror 25, transmitted through the lens 23, reflected by the half mirror 26, transmitted through the lens 21, and photo-received on the image-pickup element 22. In the preferred embodiment of the present invention, the image-pickup element 22, in addition to picking up the anterior segment image, detects an image of the ring-pattern target and an image of the target for alignment in the X and Y directions which are projected onto the cornea Ec.

The optical system 1, which is arranged on the optical axis L1, includes an optical system 2 which has an infrared light source 2a and projects a measurement target (projects measurement light) onto the fundus Ef, an optical system 3 which has a photodetector 3a and detects an image of the measurement target projected onto the fundus Ef (photo-receives the measurement light reflected from the fundus Ef), a half mirror 4, and an objective lens 6. Incidentally, examples of an optical system for measuring eye refractive power distribution or wavefront aberration include an optical system based on a phase difference method (for example, see U.S. Pat. No. 5,907,388 corresponding to Japanese Patent Application Unexamined Publication No. Hei10-108837), and an optical system based on a Shack-Hartmann method (for example, see U.S. Pat. No. 6,234,978 corresponding to Japanese Patent Application Unexamined Publication No. Hei10-216092).

The dichroic mirror 25 has a property of transmitting and reflecting the light from the light source 2a in a predetermined proportion, and reflecting each light from the light sources 13, 15, 30, and 41. The dichroic mirror 27 has a property of transmitting visible light (the light from the light source 30) and reflecting infrared light (the light from the light source 41).

A calculation and control part 70 obtains a corneal shape (corneal curvature distribution) of the eye E based on the ring-pattern target image detected by the image-pickup element 22. The calculation and control part 70 also obtains the eye refractive power distribution or the wavefront aberration of the eye E based on the measurement target image detected by the photodetector 3a. Moreover, the calculation and control part 70 obtains alignment states of the apparatus (the optical axis L1) in the X and Y directions with respect to the eye E, based on the alignment target image detected by the image-pickup element 22, and obtains an alignment state of the apparatus in the Z direction with respect to the eye E, based on the alignment target image detected by a position detector of the optical system 45b. The calculation and control part 70 controls a monitor 75 to display the anterior segment image picked up by the image-pickup element 22, a measurement result on the corneal shape, a measurement result on the eye refractive power distribution or the wavefront aberration, and others. Each measurement result can be displayed as a mapping image.

In addition, the calculation and control part 70, which controls the whole apparatus, is connected with a memory 72, an input part 74 which has various switches, a joystick 5 for alignment operation, a measurement starting switch 5a, and others.

Figure 2:
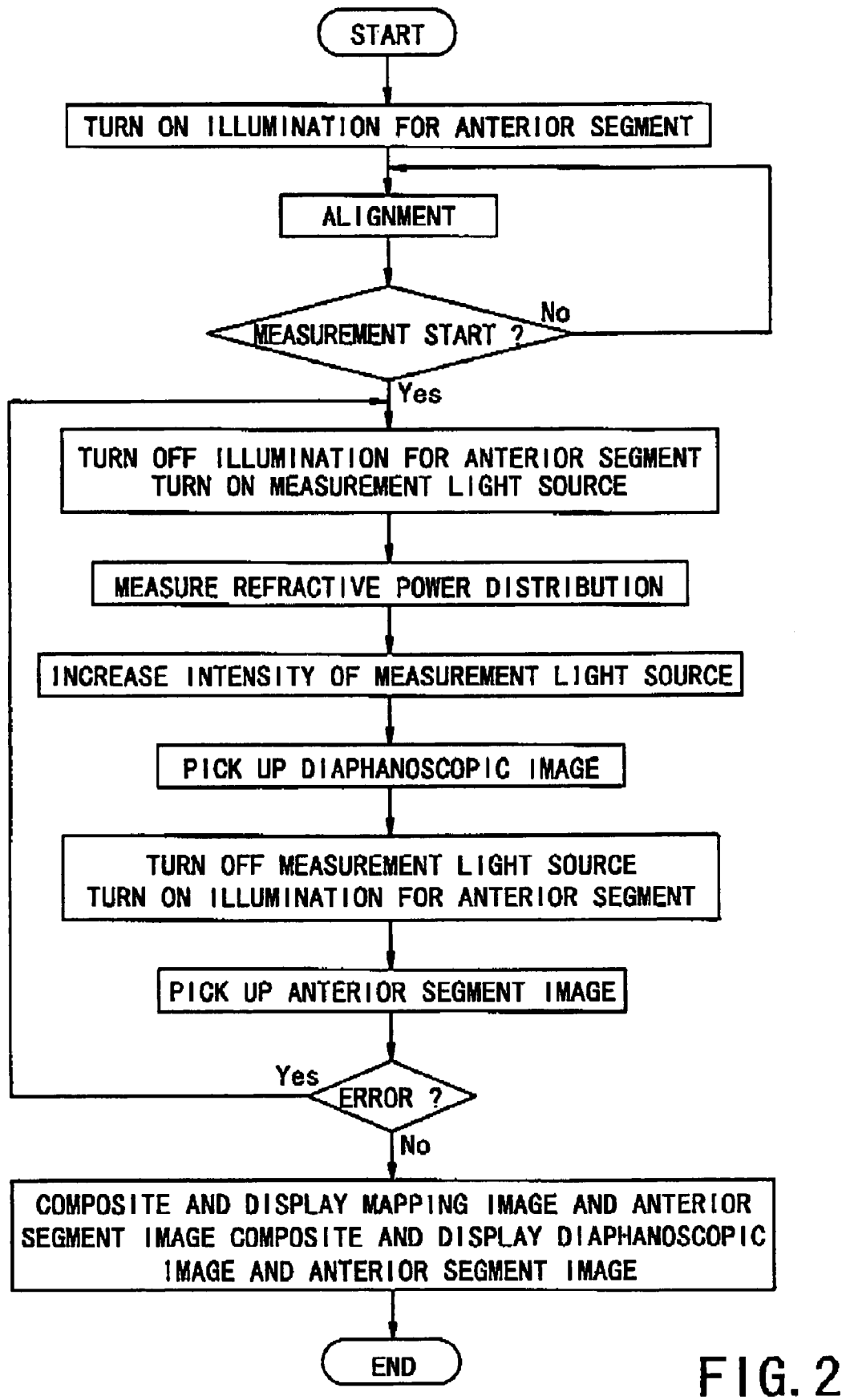
FIG. 2 is a flowchart illustrating operations of the apparatus according to the present invention.

Operations of the apparatus having the configuration as above are described below based on a flowchart in FIG. 2. Hereinbelow, described will be a case in which an eye refractive power distribution measurement mode is set by the input part 74.

First, a face of the examinee is fixed to an unillustrated face (head) supporting unit, and rough alignment is performed by an examiner's operating the joystick 5 while observing the anterior segment image displayed on the monitor 75 while turning on the light sources 15. When the alignment target image comes to be detected by the image-pickup element 22 and the position detector by performing the rough alignment, a detailed alignment of the apparatus in the X, Y and Z directions with respect to the eye E is performed by controlling an unillustrated movement mechanism part. When the alignment states in the X, Y and Z directions become appropriate, a trigger signal for measurement start is automatically generated (alternatively, the trigger signal for measurement start is generated by the switch 5a).

When the trigger signal for measurement start is generated, the calculation and control part 70 turns off or dims the light sources 15 and turns on the light source 2a so as to measure the eye refractive power distribution. In this case, the calculation and operation part 70 first performs preliminary measurement and then moves the light source 31 and the fixation target plate 32 based on an obtained measurement result in order to perform main measurement under a condition where the eye E is fogged. The calculation and control part 70 obtains the eye refractive power distribution based on a signal from the photodetector 3a and stores the eye refractive power distribution in the memory 72.

After completing the eye refractive distribution measurement, the calculation and control part 70 increases intensity of the light source 2a and performs diaphanoscopic image photographing. The light from the light source 2a is reflected from the fundus Ef and passes through a pupil of the eye E. A part of the light is reflected by the dichroic mirror 25, transmitted through the lens 23, reflected by the half mirror 26, transmitted through the lens 21, and photo-received on the image-pickup element 22. When the light, which is emitted from the light source 2a and is reflected from the fundus Ef, illuminates the vicinity of a crystalline lens of the eye E from the fundus Ef side, a diaphanoscopic image is picked up such that a low brightness portion is present at an opaque part of the crystalline lens caused by cataract.

It is preferable that the diaphanoscopic image photographing is performed at a timing when the pupil becomes larger. The calculation and control part 70 performs image processing on the diaphanoscopic image picked up by the image-pickup element 22 and extracts a rim of the pupil so as to obtain a pupil diameter based on the extracted rim. The calculation and control part 70 then determines whether or not the obtained pupil diameter is beyond a predetermined permissible range, and stores the diaphanoscopic image in the memory 72 if it satisfies this determination criterion.

After completing the diaphanoscopic image photographing, the calculation and control part 70 turns off the light source 2a, and turns on the light sources 15 again, so as to perform anterior segment image photographing. The calculation and control part 70 controls the memory 72 to store the anterior segment image picked up by the image-pickup element 22.

Figure 3A:
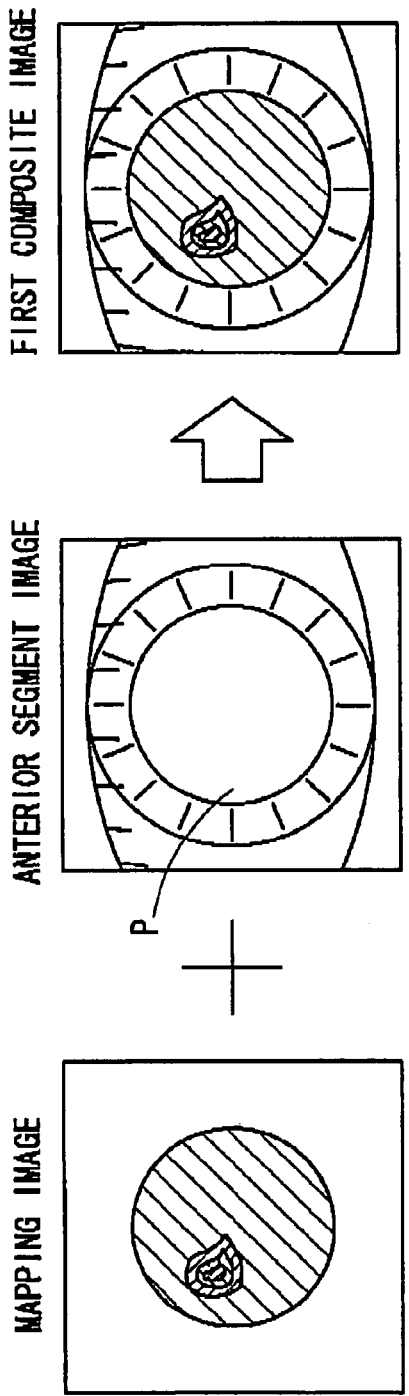
FIG. 3A is a view illustrating obtainment of a first composite image of a mapping image and an anterior segment image.
Figure 3B:
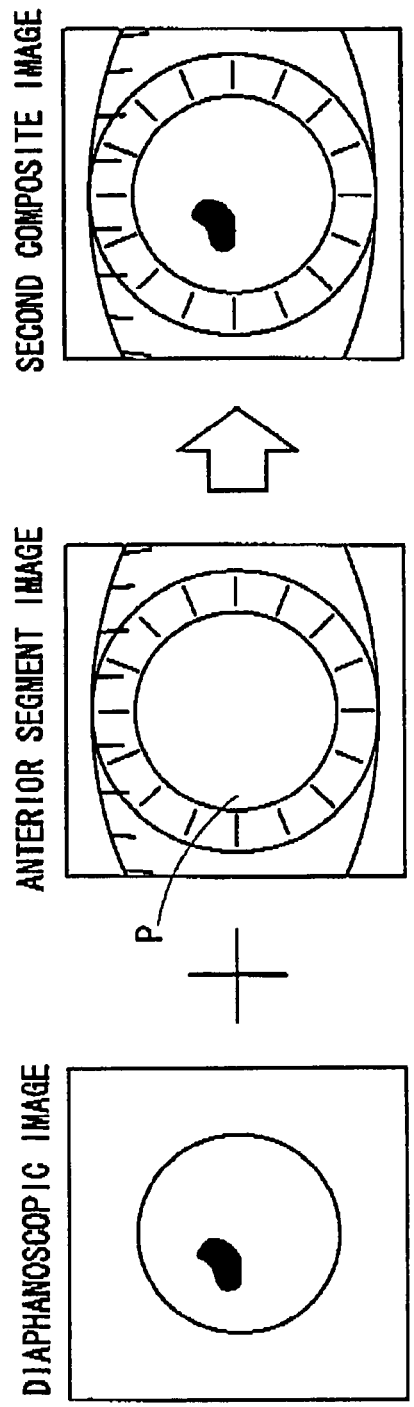
FIG. 3B is a view illustrating obtainment of a second composite image of a diaphanoscopic image and the anterior segment image.

When the eye refractive power distribution measurement, the diaphanoscopic image photographing, and the anterior segment image photographing are completed as described above, the calculation and control part 70 obtains the mapping image by performing calculation processing on the eye refractive power distribution stored in the memory 72. In this mapping image, eye refractive power is color-coded according to predetermined ranges of diopter. In addition, a first composite image is obtained by superimposing the obtained mapping image and the anterior segment image stored in the memory 72 through image processing. Furthermore, a second composite image is obtained by superimposing the diaphanoscopic image and the anterior segment image stored in the memory 72 through image processing. In this process, the calculation and control part 70 may, for example, affix the mapping image or the diaphanoscopic image to a pupillary area P of the anterior segment image as shown in FIGS. 3A and 3B. It is preferable that the mapping image or the diaphanoscopic image and the anterior segment image are superimposed in a state where corneal center positions thereof, which correspond to a detection position of the alignment target image formed by the light source 41, coincide with a predetermined display reference position, or the diaphanoscopic image detected through image processing and the anterior segment image are superimposed in a state where pupil center positions thereof coincide with the predetermined display reference position. This is because an alignment deviation in the X and Y directions due to difference in measurement timing can be corrected.

Figure 4:
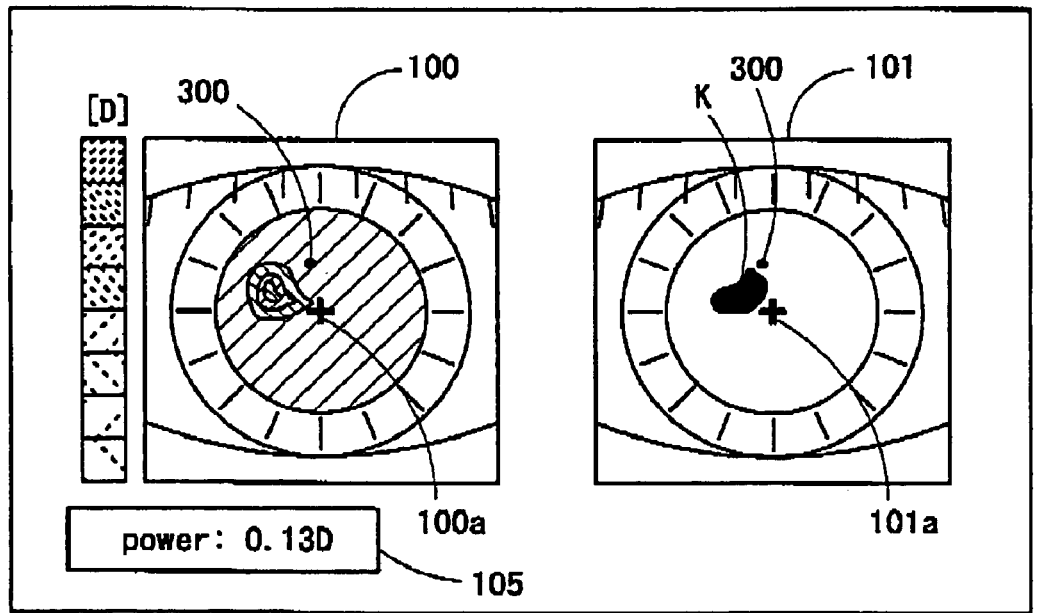
FIG. 4 is a view showing an example in which the first composite image and the second composite image are displayed side by side.

FIG. 4 shows an example where a first composite image 100 and a second composite image 101 obtained by the calculation and control part 70 are displayed side by side on the monitor 75. It is preferable that the corneal center positions (or the pupil center positions) of the first composite image 100 and the second composite image 101, which correspond to the detection position of the alignment target image formed by the light source 41, coincide with center marks 100a and 101a respectively. This is because the alignment deviation in the X and Y directions due to the difference in measurement timing can be corrected.

In the example shown in FIG. 4, an opaque part K is observed in the second composite image 101. In the first composite image 100, the eye refractive power in a part corresponding to the opaque part K of the second composite image 101 is displayed in different colors from a color of the surrounding area. By displaying the first composite image 100 and the second composite image 101, i.e., the mapping image and the diaphanoscopic image, side by side, a positional relationship between an unusual part of the mapping image and the opaque part of the diaphanoscopic image can be checked. Furthermore, if there is no opaque part in the diaphanoscopic image even though the unusual part is present in the mapping image, it can be confirmed that error in the measurement is caused by a different factor. By illuminating the crystalline lens from the interior of the eye so as to pick up the diaphanoscopic image as described above, it is possible to pick up an image of an inserted intraocular lens in addition to the opaque part caused by cataract, and by displaying the image of the intraocular lens on the monitor 75, the position of the intraocular lens can be ascertained.

By moving a mouse 301 which is connected to the calculation and control part 70, a cursor 300 can synchronously move on the first composite image 100 and the second composite image 101, and an arbitrary point on the first composite image 100 or the second composite image 101 can be selected. By selecting the arbitrary point, an eye refractive power value 105 at the arbitrary point on the first composite image 100 or the second composite image 101 is displayed.

In the description above, the first composite image 100 (the mapping image of the eye refractive power distribution) and the second composite image 101 (the diaphanoscopic image) are displayed side by side on one screen of the monitor 75. However, a third composite image, which is generated by superimposing a mapping image of the cornea shape obtained from the ring pattern target image which is picked up by the image-pickup element 22 and the anterior segment image may be displayed side by side on the screen of the monitor 75. The third composite image is also displayed in a manner that a corneal center position thereof (or a pupil center position thereof), which corresponds to the detection position of the alignment target image formed by the light source 41, coincides with a center mark. Accordingly, useful information in diagnosis of the examinee's eye can be obtained from the images.

In addition, the diaphanoscopic image photographing is performed subsequent to the eye refractive power distribution measurement in the description above, however, the diaphanoscopic image photographing may be performed before or during the eye refractive power distribution measurement. Furthermore, the three operations including the eye refractive power measurement, the diaphanoscopic image photographing, and the anterior segment image photographing are performed successively by one trigger signal in the description above, however, each operation may be performed by an independent trigger signal, or the operations may be performed in combination.

Figures 5A, 5B:
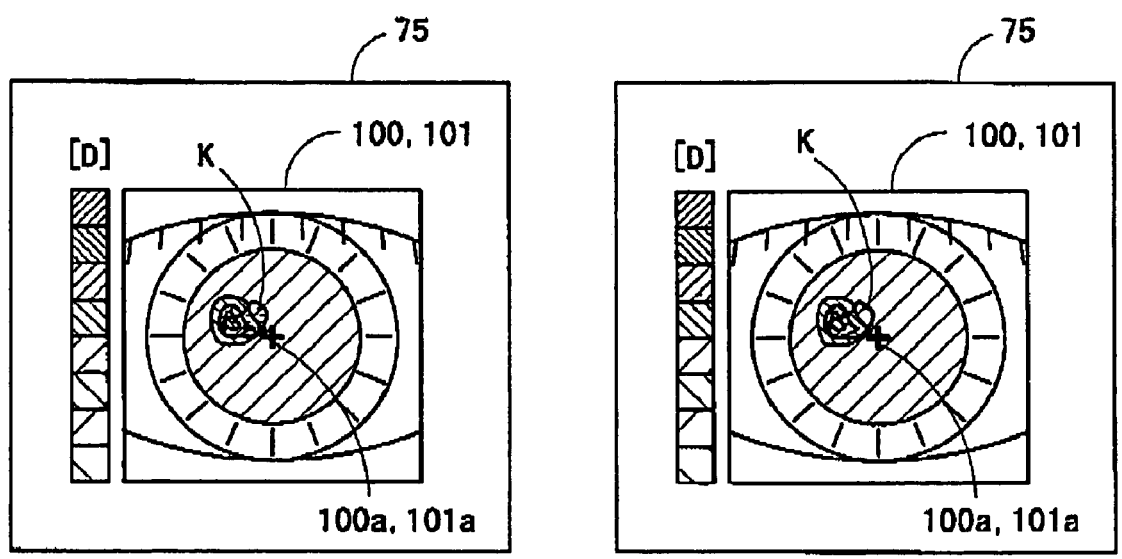
FIGS. 5A and 5B are views showing an example in which the first composite image and the second composite image are displayed as a composite image.

Besides, the first composite image 100 and the second composite image 101 are displayed side by side in the description above, however, they may be superimposed and displayed as a composite image. For example, it is preferable that the second composite image 101 which is displayed translucently is superimposed on the first composite image 100 so as to be displayed as a composite image after adjusting their positional relationship (see FIG. 5A). Alternatively, it is preferable that the opaque part K of the second composite image 101 is extracted by image processing, only an edge of the opaque part K is presented in the second composite image 101, and the second composite image 101 is superimposed on the first composite 100 so as to be displayed as a composite image after adjusting their positional relationship (see FIG. 5B).

In addition, the light source 2a (optical system) which projects the measurement light, is used as the light source (optical system) which projects the light for the diaphanoscopic image photographing in the description above, however, an infrared light source (optical system) dedicated for the diaphanoscopic image photographing may be provided.

Furthermore, the image pickup element 22 (optical system), which picks up the anterior segment image, is used as the image pickup element for picking up the diaphanoscopic image in the description above, however, an image-pickup element (optical system) dedicated for the diaphanoscopic image photographing may be provided.

According to the preferred embodiment of the present invention, by displaying the diaphanoscopic image, which is picked up when the anterior segment illumination (the light source 15) is turned off or dimmed, and the anterior segment image, which is picked up when the anterior segment illumination is turned on, the position of the opaque part in the pupil can be appropriately ascertained from the positional relationship of the diaphanoscopic image on the anterior segment image and others. In addition, since noise caused by the anterior segment illumination is suppressed in the diaphanoscopic image, the diaphanoscopic image is displayed clearly with good contrast. Moreover, by picking up the diaphanoscopic image and the anterior segment image at different times, difficulty in recognizing the rim of the pupil resulting from degraded contrast between an image inside the pupil (the diaphanoscopic image) and an image outside the pupil due to automatic gain control of the image-pickup element 22 and others is resolved. However, some degree of advantages can be obtained even if the diaphanoscopic image and the anterior segment image are simultaneously picked up with the anterior segment illumination turned on.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
   a measurement optical system for projecting measurement light onto a fundus of an examinee's eye and photo-receiving the measurement light reflected from the fundus so as to measure eye refractive power distribution or wavefront aberration of the eye;
   an illumination for an anterior segment of the eye;
   a first image-pickup optical system for picking up an image of the anterior segment;
   a projection optical system for projecting photographing light onto the fundus;
   a second image-pickup optical system for photo-receiving the photographing light reflected from the fundus so as to pick up a diaphanoscopic image of the eye;
   a monitor;
   a calculation part for obtaining a mapping image based on a measurement result obtained by the measurement optical system; and
   a control part for displaying the mapping image and the diaphanoscopic image on one screen of the monitor.

2. The ophthalmic apparatus according to claim 1, wherein the control part displays the mapping image and the diaphanoscopic image side by side or as a composite image on the screen of the monitor.

3. The ophthalmic apparatus according to claim 2, wherein the control part displays the mapping image and the diaphanoscopic image after adjusting positions thereof based on corneal center positions or pupil center positions obtained from the images.

4. The ophthalmic apparatus according to claim 1, wherein the control part displays a first composite image of the mapping image and the anterior segment image, and a second composite image of the diaphanoscopic image and the anterior segment image side by side or as a composite image on the screen of the monitor.

5. The ophthalmic apparatus according to claim 4, wherein the control part displays the first composite image and the second composite image after adjusting positions of the images based on corneal center positions or pupil center positions of the images.

6. The ophthalmic apparatus according to claim 1, wherein the first image-pickup optical system and the second image-pickup optical system share an image-pickup element.

7. The ophthalmic apparatus according to claim 1, wherein the measurement optical system and the projection optical system share a light source, and
   the control part increases intensity of the light source when projecting the photographing light with respect to intensity of the light source when projecting the measurement light.

8. The ophthalmic apparatus according to claim 1, wherein the control part turns off or dims the illumination for the anterior segment when picking up the diaphanoscopic image.

* * * * *